US008912006B2

(12) United States Patent
Achyuta et al.

(10) Patent No.: US 8,912,006 B2
(45) Date of Patent: Dec. 16, 2014

(54) MICROFLUIDIC DEVICE FOR GENERATING NEURAL CELLS TO SIMULATE POST-STROKE CONDITIONS

(71) Applicants: The Charles Stark Draper Laboratory, Inc., Cambridge, MA (US); The University of South Florida, Tampa, FL (US)

(72) Inventors: Anilkumar Harapanahalli Achyuta, Cambridge, MA (US); Javier Cuevas, Lutz, FL (US); Shivshankar Sundaram, Tampa, FL (US); Chris Katnik, Wesley Chapel, FL (US)

(73) Assignees: The Charles Stark Draper Laboratory, Inc., Cambridge, MA (US); The University of South Florida, Tampa, FL (US)

( * ) Notice: Subject to any disclaimer, the term of this patent is extended or adjusted under 35 U.S.C. 154(b) by 0 days.

(21) Appl. No.: 13/758,572

(22) Filed: Feb. 4, 2013

(65) Prior Publication Data

US 2013/0203086 A1    Aug. 8, 2013

Related U.S. Application Data

(60) Provisional application No. 61/594,668, filed on Feb. 3, 2012.

(51) Int. Cl.
*G01N 33/50* (2006.01)
*C12M 1/34* (2006.01)
*C12M 3/06* (2006.01)
*G01N 21/64* (2006.01)

(52) U.S. Cl.
CPC ........ *G01N 21/6486* (2013.01); *G01N 33/5005* (2013.01); *C12M 41/34* (2013.01); *G01N 33/5058* (2013.01); *C12M 23/16* (2013.01)
USPC .......... 436/151; 435/287.1; 436/63; 436/149; 422/82.01; 422/82.02

(58) Field of Classification Search
CPC .... C12M 1/3407; C12M 23/16; G01N 27/04; G01N 33/50; G01N 33/5005; G01N 33/5008; G01N 33/5044; G01N 33/5058
See application file for complete search history.

(56) References Cited

U.S. PATENT DOCUMENTS

| 2003/0143720 | A1* | 7/2003 | Hickman | 435/287.1 |
| 2005/0221282 | A1* | 10/2005 | Owen et al. | 435/4 |
| 2006/0154361 | A1* | 7/2006 | Wikswo et al. | 435/289.1 |
| 2007/0037225 | A1* | 2/2007 | Metzger et al. | 435/7.22 |
| 2007/0148139 | A1 | 6/2007 | Vacanti et al. | |
| 2009/0042288 | A1* | 2/2009 | Stoppini | 435/374 |

OTHER PUBLICATIONS

Holmes, David et al. "Leukocyte analysis and differentiation using high speed microfluidic single cell impedance cytometry", Lab on a Chip, Royal Society of Chemistry, vol. 9, No. 20, Jan. 1, 2009, pp. 2881-2889.
Kumar, A. et al., "A modular approach to create a neurovascular unit-on-a-chip", Lab Chip, vol. 13, Jan. 1, 2013, pp. 542-553.
Yang, L. et al., "An in vitro model of ischemic stroke", Methods in Molecular Biology, vol. 814, Jan. 1, 2012, pp. 451-466.
Borenstein J et al. "Microfabrication Technology for Vascularized Tissue Engineering", Biomedical Microdevices 4(3) 167-175 (2002).

* cited by examiner

*Primary Examiner* — Melanie Y Brown
*Assistant Examiner* — Rebecca Martinez
(74) *Attorney, Agent, or Firm* — Edward A. Gordon; Foley & Lardner LLP

(57) ABSTRACT

This application provides devices for modeling ischemic stroke conditions. The devices can be used to culture neurons and to subject a first population of the neurons to low-oxygen conditions and a second population of neurons to normoxic conditions. The neurons are cultured on a porous barrier, and on the other side of the barrier run one or more fluid-filled channels. By flowing fluid with different oxygen levels through the channels, one can deliver desired oxygen concentrations to the cells nearest those channels.

18 Claims, 12 Drawing Sheets

MICROFLUIDIC DEVICE FOR GENERATING NEURAL CELLS TO SIMULATE POST-STROKE CONDITIONS

CROSS-REFERENCE TO RELATED PATENT APPLICATIONS

This application claims priority to Provisional U.S. Patent Application 61/594,668, filed Feb. 3, 2012, which is incorporated herein by reference in its entirety.

BACKGROUND OF THE DISCLOSURE

Ischemic stroke occurs when neural tissue is damaged due to low oxygen levels. Magnetic resonance imaging detects three distinct areas in the brain of a stroke patient. The first, called the core, is the area that receives little or no oxygen, and experiences severe necrosis. A second area consists of normal tissue that receives sufficient oxygen. The third area falls between the core and the normal tissue, and is called the penumbra. Functionally, the penumbral area has compromised blood flow (CBF) and decreased oxygen consumption ($CMRO_2$), which translates into neurons that are still viable but stressed. Over the course of several days following a stroke, the core gradually expands into the penumbra. Treatments for ischemic stroke are extremely limited, in part because of the lack of adequate in vitro models for ischemic stroke. There is a need in the art for an ischemic stroke model that allows one not only to study the basic biology of the core and penumbra but to test novel therapeutic interventions.

SUMMARY OF THE DISCLOSURE

This application provides devices for modeling ischemic stroke conditions. The devices can be used to culture neurons and to subject a first population of the neurons to low-oxygen conditions and a second population of neurons to normoxic conditions. The neurons are cultured on a porous barrier, and on the other side of the barrier run one or more fluid-filled channels. By flowing fluid with different oxygen levels through the channels, one can deliver desired oxygen concentrations to the cells nearest those channels. The devices herein provide in vitro models for a number of in vivo medical conditions.

According to one aspect of the disclosure, a device for modeling ischemic stroke conditions includes a fluid-containing chamber; a porous barrier to which the cells are adhered; and a first channel having an inlet and an outlet, separated from the chamber and cells by the porous barrier, wherein the cells comprise a first population that is proximal to the first channel and a second population that is distal from the first channel. The device also includes a first array of electrodes positioned between the first channel and the porous barrier and aligned along the length of the first channel; and a second array of electrodes coupled to the fluid facing side of the roof of the fluid-containing chamber.

In certain implementations, the fluid-containing chamber includes cells. The cells can include central nervous system cells, cardiac muscle cells, or tumor cells. The central nervous system cells can include neurons, microglia, astrocytes, oligodendrocytes, or neural progenitors. In other implementations, the cells include a monolayer of muscle cells or endothelial cells along at least one wall of the channel. In yet other implementations, the cells are organized as a three-dimensional culture. In some implementations, the first population of cells are less than 100 microns apart. In certain implementations, immune cells are disposed in the channel.

In some implementations, the first channel is adapted for flowing fluid along the barrier, and the cells experience substantially no shear stress when fluid flows through the first channel. In other implementations, the electrodes are between about 100 µm and 150 µm in diameter and configured to measure trans-endothelial electrical resistance.

In yet other implementations, the device also includes a second channel configured for fluid flow, wherein the porous barrier separates the second channel from the chamber and the cells. In some of these implementations, the first channel contains a first fluid and the second channel contains a second fluid. The first fluid and the second fluid can have different levels of oxygen or oxygen scavenger. In some implementations, the flow of fluid through the first and second channel is independently controllable. The porous barrier is sufficiently transparent to allow microscopy of the cells in some implementations. In some implementations, the device further includes a proteinaceous coating that is adhered to the porous membrane.

According to another aspect of the disclosure, a for modeling ischemic stroke conditions includes a cellular chamber made of a material suitable for cell culture; a base comprising a channel, wherein the channel has an inlet and an outlet, and the channel is sized to be proximal to a first region of the cellular chamber and distal from a second region of the cellular chamber; a porous membrane suitable as a substrate for cell culture, wherein the porous membrane is sized to separate the channel from the cellular chamber; a plurality of electrodes configured to measure trans-endothelial electrical resistance; and a means for securing the microporous membrane between the chamber and the channel.

In some implementations, the kit also includes a trans-endothelial electrical resistance module, an atmospheric control system and/or a controller.

According to one aspect of the disclosure, a method for modeling ischemic conditions includes providing a microfluidic device including a fluid-filled chamber, a channel, a porous barrier separating the chamber from the channel, a first population of CNS cells proximal to the channel, and a second population of CNS cells distal from the channel. The first population of the cells is then exposed to a low concentration of oxygen, and the second population of the cells is exposed to a higher concentration of oxygen; thereby modeling the ischemic condition. The method also includes measuring at least one cellular property, such as a cellular factor.

In some implementations, the ischemic condition is ischemic stroke and the cells can include central nervous system cells such as neurons, microglia, astrocytes, oligodendrocytes, or neural progenitors.

In other implementations, a third population of CNS cells is disposed between the first population and the second population, and the third population of CNS cells models a penumbra produced by an ischemic stroke.

In certain implementations, the method also includes measuring trans-endothelial electrical resistance across the cells, visualizing the cells in the device by microscopy, and/or removing the cells from the device and performing biochemical analysis or microscopy on the removed cells.

In some implementations, the method of measuring the at least one cellular property further includes testing for a factor secreted by the cells. The factor can be measured from the chamber and/or one of the channels.

In other implementations, exposing the first population of cells to a lower concentration of oxygen includes delivering an oxygen scavenger through the channel within an effective distance of the first population of cells. Exposing the second population of cells to a high concentration of oxygen includes delivering oxygenated fluid through the channel within an effective distance of the second population of cells.

The cells are exposed to a test agent in some implementations. The test agent can be selected such that it promotes neurodegeneration, necrosis, or apoptosis. In other implementations, the agent is a cancer cell capable of invading neural tissue.

BRIEF DESCRIPTION OF THE DRAWINGS

The skilled artisan will understand that the figures, described herein, are for illustration purposes only. It is to be understood that in some instances various aspects of the described implementations may be shown exaggerated or enlarged to facilitate an understanding of the described implementations. In the drawings, like reference characters generally refer to like features, functionally similar and/or structurally similar elements throughout the various drawings. The drawings are not necessarily to scale, emphasis instead being placed upon illustrating the principles of the teachings. The drawings are not intended to limit the scope of the present teachings in any way. The system and method may be better understood from the following illustrative description with reference to the following drawings in which.

DETAILED DESCRIPTION

The various concepts introduced above and discussed in greater detail below may be implemented in any of numerous ways, as the described concepts are not limited to any particular manner of implementation. Examples of specific implementations and applications are provided primarily for illustrative purposes.

Ischemic stroke produces a region of tissue at the site of the ischemic region, called the core, that includes necrotic neural tissue. Surrounding the core is the penumbra, a region of neural tissue that is less strongly affected by the disrupted oxygenation. One of the goals of stroke therapy is to prevent expansion of the core by enhancing survival of cells in the penumbra. To date, only a single drug has been approved for the treatment of acute ischemic stroke. This drug, tissue plasminogen activator (tPA), is subject to significant limitations that result in less than 3% of stroke victims receiving this thrombolytic. A major impediment in the development of novel drug therapies for minimizing stroke injury is that the mechanisms that contribute to progression of the stroke lesion remain poorly understood. Moreover, the interaction between cells in the ischemic core, penumbra, and normal regions have not been mimicked or studied sufficiently in real time to fully comprehend how these interactions influence expansion of the lesion.

This disclosure provides a model device that generates accurate ischemic conditions in vitro to facilitate fundamental understanding of cellular communication between necrotic core and the ischemic penumbra. The device is also suitable as screening tool for therapeutic interventions. In particular, this application discloses a device that generates normoxic, anoxic, and hypoxic environments closely communicating with each other to replicate the in vivo conditions that occur during ischemic stroke.

I. Non-cell Components of the Ischemic Stroke Model

Figure 1A:
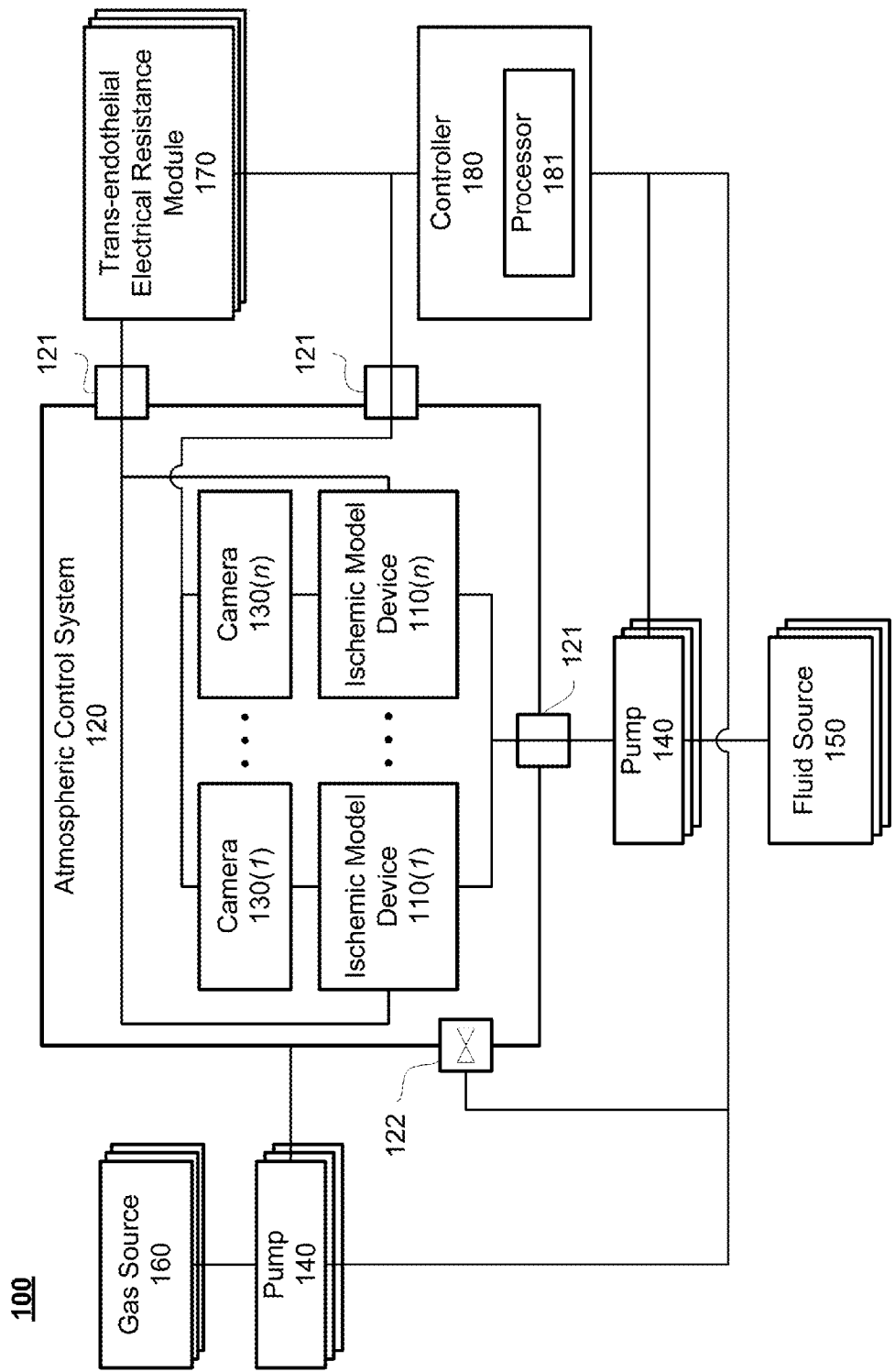
FIG. 1A is a schematic illustration of a system for modeling ischemic stroke; according to one implementation of the disclosure.

FIG. 1A illustrates a system 100 for modeling ischemic stroke. The system 100 includes an atmospheric control system (ACS) 120. Within the ACS 120 the system includes at least one camera 130 and at least one ischemic model device 110. The ACS 120 also includes a plurality of access ports 121 and access valves 122. A first set of pumps 140 flow fluid from at least one fluid source 150 through the plurality of ischemic model devices 110. A second series of pumps 140 flow gas from a gas source 160 into the ACS 120. System 100 also includes a trans-endothelial electrical resistance (TER) module 170. The system 100 further includes a controller 180 with at least one processor 181 for controlling the components of system 100.

Referring to system 100, and in greater detail, the ACS 120 maintains proper atmospheric conditions for ischemic stroke experimentation. In some implementations, the ACS 120 maintains a specific experimental temperature, pressure, gas mixture, humidity, or any combination thereof within the testing area. The ACS 120 is connected to a plurality of gas sources 160. To maintain specific gas mixtures, the ACS 120 pumps gases into the ACS 120 with a pump 140. The ACS 120 also controls a pressure valve 122 such that a constant pressure may be maintained within the ACS 120. For example, the ACS 120 may maintain a constant 37° C. temperature and 5% carbon dioxide concentration. In some implementations, the ACS 120 is an incubator.

Within the ACS 120 there are a plurality of ischemic model devices 110 and cameras 130. The ischemic model device 110 is discussed further in relation to FIG. 1B, but briefly, the ischemic model flow device 110 is a microfluidic flow device configured to model ischemic injuries. The cameras 130 are placed such that they can view the cells within the ischemic model device 100. In some implementations, the cameras 130 are part of a microscope, and may be configured to capture fluorescence images of the cells. In some implementations, the camera 130 is placed outside ACS 120 and views the ischemic model devices 110 and/or cells through a window in the ACS 120. Access ports 121 are positioned around the housing of the ACS 120 such that cables, connectors, and flow tubing can pass into and out of the ACS 120 without disturbing the controlled atmospheric conditions.

As illustrated, system 100 includes at least one TER module 170. The TER module 170 is configured to measure the trans-endothelial electrical resistance across the cells in the ischemic model device 110. In some implementations, trans-endothelial electrical resistance is a measure of the severity of damage caused by an ischemic event. In other implementations, the TER module 170 may be replaced or supplemented with other test equipment to monitor the cellular health within the ischemic model devices 110.

The system 100, as illustrated, also includes a plurality of fluid pumps 140 and a fluid source 150. In some implementations, fluid from a fluid source 150 may be forced through the ischemic model devices 110 by a pump 140. The fluid source contains, in some implementations, a therapeutic agent as described below. In certain implementations, the oxygen levels with the fluid have been altered such that the fluid causes a portion of the cells within the ischemic model device 110 to become ischemic.

Figure 1B:
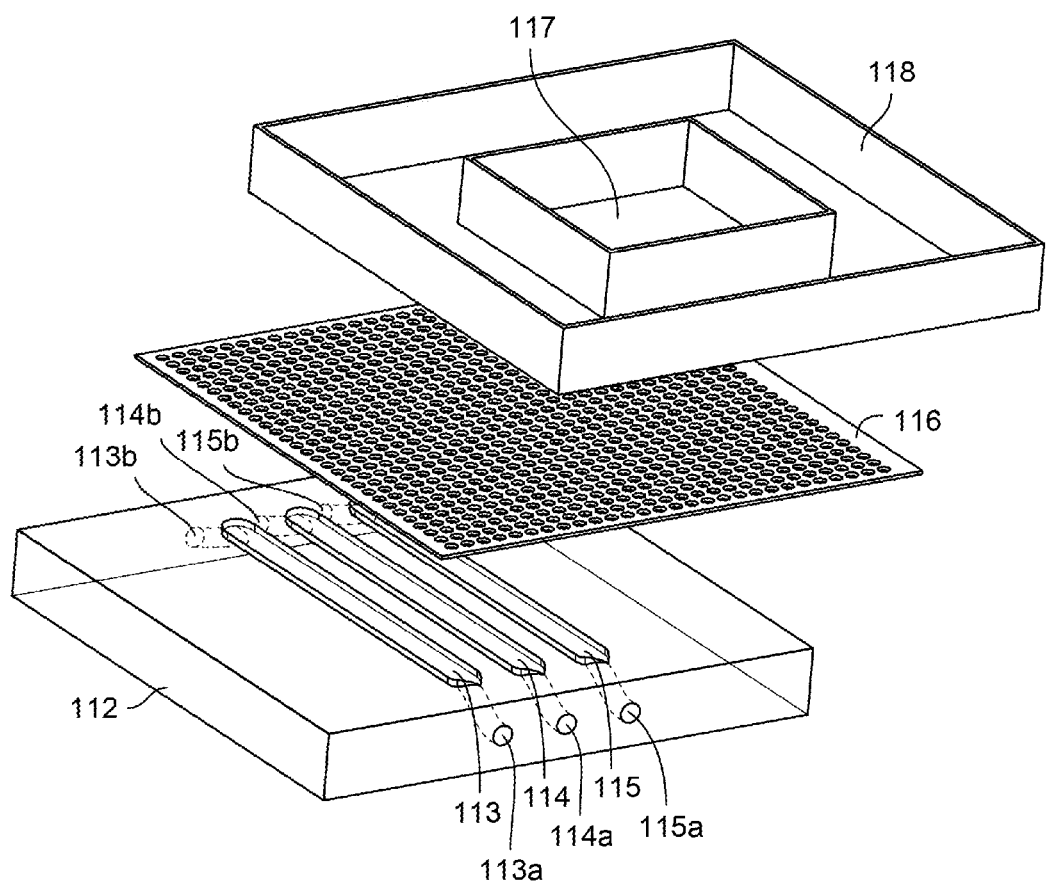
FIG. 1B illustrates an exploded view of an ischemic model device such that can be used in the system of FIG. 1A; according to one implementation of the disclosure.

FIG. 1B is an exploded view of the ischemic model device 110 discussed above. The model 110 includes a chamber 117 in which cells (such as neurons) are cultured. Surrounding the chamber 117 is a chamber wall 118 capable of containing cell culture medium. One side of the chamber (for instance, the bottom) is formed by a porous barrier 116. Cells grown in the chamber can adhere to the porous barrier 116. The porous barrier 116 separates the chamber 117 from the base 112.

The base 112 includes three parallel channels 113, 114, and 115. Each channel has an inlet 113a, 114a, or 114a through which fluid can enter, and an outlet 113b, 114b, or 115b, through which fluid can exit. In some implementations, a user pumps fluid through the channels using a peristaltic pump. In some implementations, a different fluid is pumped through each channel. As illustrated, the base 112 does not completely enclose the channels; rather, the roof of each channel is provided by the porous barrier 116.

In this arrangement, when a solution is pumped through the channels, solutes can pass through the porous barrier and reach the cells. Because the concentration of any solute may be highest near the channel through which it is delivered, the cells closest to that channel may receive the highest dose of that solute, while cells farther from that channel may receive lower doses. Channels can deliver solutes such as oxygen scavengers. Examples of oxygen scavengers are $Na_2SO_3$, sodium lactate, and EC-Oxyrase. In some implementations, channels deliver oxygen, small organic molecules, macromolecules, and/or cells.

Figure 2:
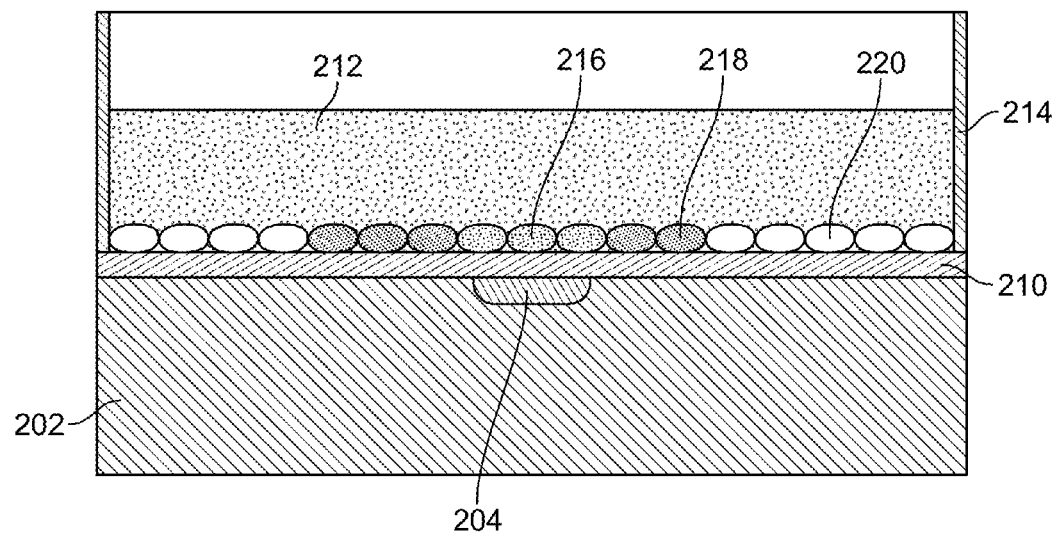
FIG. 2 is a side view of an ischemic model device comprising CNS cells; according to one implementation of the disclosure.

FIG. 2 illustrates a side view of a single channel ischemic model device 200. The base 202 of the device has a single channel 204. Above the base 202 and channel 204 is the porous barrier 210. Cultured cells adhere to the barrier, and these cells can be divided into three categories based on their position relative to the channel 204. The first population 216 (also referred to as the "proximal cells") is proximal to the channel and is shaded black. The second population 220 (also referred to as the "distal cells") is distal to the channel and is shown in white. There is also a population of cells 218 (also referred to as "intermediate cells") shaded gray that lies between the proximal and distal populations. The cells are submerged in a solution 212 that allows the cells to remain viable at least over the course of an experiment.

In some implementations, the device 200 is used to create a two dimensional model of ischemia. For example, if the channel 204 is filled with a high-oxygen fluid and the solution 212 has lower oxygen levels, the proximal cells 216 will receive high oxygen levels, the intermediate cells 218 will receive intermediate oxygen levels, and the distal cells 220 will receive low oxygen levels. If, on the other hand, the channel 204 is filled with a low-oxygen fluid or an oxygen scavenger, the proximal cells 216 will experience low oxygen levels, the intermediate cells 218 will experience intermediate oxygen levels, and the distal cells will experience high oxygen levels. In such a scenario, the proximal cells 216 would model the core of an ischemic stroke, the intermediate cells 218 would model the penumbra, and the distal cells 220 would model the healthy tissue. In some implementations, the base layer 202 includes multiple channels 204.

In some implementations, the proximal cells are within about 100 μm of a channel 204. In certain implementations, the proximal cells are within about 300, 200, 100, 75, or 50 μm of a channel 204. In certain implementations, the distal cells are more than 200 μm, 500 μm, 1 mm, 2 mm, or 5 mm from the channel 204. In some implementations, a cell is proximal to a channel 204 if the cell receives an effective dose of the substance being delivered by the channel.

The chamber walls of the device are made of a material suitable for cell culture. The material is strong enough to support the tissue culture media, non-toxic to cells, and substantially non-reactive with the other components of the device. Examples of appropriate cell culture materials include polymeric and/or non-polymeric materials, including PDMS, acrylic, polyethylene, polyolefin polymer, polyurethane, polystyrene, Pyrex, glass, polypropylene, or Permanox.

The chamber is a suitable size for culturing cells. In some implementations, the chamber accommodates a cell culture area of ~0.5 $cm^2$, close to the surface area of a section of adult rat brain. In some implementations, the cell culture area is approximately 0.01-0.02 $cm^2$, 0.02-0.05 $cm^2$, 0.05-0.1 $cm^2$, 0.1-0.2 $cm^2$, 0.2-0.5 $cm^2$, 0.5-1 $cm^2$, 1-2 $cm^2$, 2-5 $cm^2$, or 5-10 $cm^2$. The chamber walls are high enough to allow the chamber to be filled with sufficient medium to support cell viability, growth, or metabolism.

The chamber can be filled with a liquid compatible with cell metabolism and/or growth. Suitable media for neuronal cultures include Dulbecco's modified Eagle's medium supplemented with 10% (v/v) fetal calf serum, 100U/ml penicillin, and 0.1 mg/ml streptomycin and Neurobasal medium supplemented with B27 and 0.5 mM L-glutamine. One skilled in the art will recognize that the chamber can be filled with other liquids. In some implementations, during experiments it may be appropriate to temporarily culture the cells in a liquid that is free of macromolecules (an example is physiological saline solution (PSS)), even if it does not support long-term cell growth. A liquid free of macromolecules can facilitate detection of factors that the cells secrete during the experiment.

The amount of oxygen the solution 212 is exposed to is controlled by the ACS 120 and/or other means. For example, the ACS 120 may maintain a low oxygen concentration in the experimental chamber such that the only oxygen available to the cells is oxygen that diffuses through the pours barrier 210 from the channel 204. Additional means of controlling the oxygen available to the cells may include placing a coverslip on the surface of the liquid, closing a door in the device, or floating oil on top of the liquid.

In certain implementations, the device does not require constant perfusion of the cell culture chamber. Avoiding perfusion can prevent the washout of factors, such as cytokines, that contribute to the extracellular milieu of the penumbra. In addition, avoiding perfusion of the neural cells avoids exposing these cells to shear stress. In certain implementations, the cells are subject to shear stress forces of less than about 1, 0.5, 0.2, 0.1, 0.05, 0.02, or 0.01 dyne/cm$^2$.

The ischemic model should be maintained at a temperature compatible with cell viability, metabolism, and/or growth. Generally, incubation at 37° C. is appropriate for human cells, although in the case of temperature-sensitive human cells, higher or lower temperatures can be used.

The base is be made of a material that is strong enough to support the weight of the cell culture and is capable of being shaped to produce channels. Appropriate materials for the base include polydimethylsiloxane (PDMS), cyclic olefin copolymer (COC), and polystyrene.

In some implementations, the porous barrier includes a membrane. The membrane can serve as a substrate that supports the cells while allowing oxygen, oxygen scavengers, or other substances to travel from the channels into the cell culture chamber.

In certain implementations, the barrier's pores are small enough to prevent the neural cells from substantially colonizing the channels. In some implementations, however, the pores are large enough to allow immune cells in the channels to enter the cell culture chamber. In preferred implementations, the average pore diameter is about 10 µm, for instance between 8 µam and 12 µm.

The average pore diameter can also be about 0.4 µm, 1 µm, 2, µm, 3 µm, 5 µm, 20 µm, or 50 µm, for instance within 20% of one of those diameters. In some implementations, the pore diameters are less than about 2 nm, 5 nm, 10 nm, 20 nm, 50 nm, 100 nm, 200 nm, or 400 nm. In some implementations, the pore area constitutes about 7%, about 7-10%, or about 5-15% of the surface area of the barrier.

The thickness of the barrier can vary with the application. In some implementations, the barrier will have a thickness between 10 µm and 500 µm. In some implementations, the barrier will have a thickness between 100 nm and 500 µgm. For instance, the barrier may be 100-200 nm, 200-500 nm, 500 nm-1 µam, 1-2 µm, 2-5 µm, 5-10 µm, 10-20 µm, 20-50 µm, 50-100 µm, 100-200 µm, or 200-500 µm.

The barrier should be compatible with cell metabolism and, optionally, cell growth. The barrier should also be one to which cells can adhere. Appropriate materials for the barrier include polycarbonate (PC), polyester (e.g., polyethylene terephthalate (PET)), collagen-coated polytetrafluoroethylene (PTFE), PDMS, polysulfone, and natural electrospun ECM proteins (such as collagen). In certain implementations, the barrier is non-biodegradable over time periods typical for cell culture in a given vessel. Certain polycarbonates, polyesters, polytetrafluoroethylenes, ethylene-vinyl acetates (EVA), and polyvinyl acetates (PVA) are non-biodegradable.

Porous barriers can be produced by a number of methods. In some implementations, a polymer is initially produced in a non-porous form, and pores are produced, for example by micromachining Alternatively, the porous barrier can be produced using pore-forming agents or other suitable techniques.

In some implementations the porous barrier is made from a different material from the base. However, in other implementations, the porous barrier and the base are a single component. In such an instance, the channels run through the middle of the base, and pores in the material of the base are the conduits through which oxygen or other components travel to the cell culture chamber.

In some implementations, the cells adhere to the porous barrier. In certain implementations, a significant number of, or substantially all of, the cells are in direct contact with the porous barrier.

The barrier may also contain functional components. In some implementations, the barrier includes a moiety or component that promotes cell adhesion. This may be achieved with a proteinaceous coating such as gelatin, fibronectin, or poly-lysine. The membrane may also contain an antibiotic and/or anti-fungal agent to inhibit contamination, or one or more growth factors to promote cell growth and division.

The channels may be used to deliver oxygen to the cells. In some implementations, a channel delivers a high amount of oxygen, for example, an amount sufficient to maintain high cell viability over an extended period, modeling normoxic tissue. In some implementations, a channel delivers a low amount of oxygen, for example, an amount insufficient for high cell viability over an extended period, modeling hypoxic or anoxic tissue such as the core or penumbra. The low amount of oxygen may be less than 90%, 80%, 70%, 60%, 50%, 40%, 30%, 20%, or 10% of the high amount of oxygen.

In some implementations, the device includes a single channel. In some implementations, the device includes 2, 3, 4, 5, 6, 7, 8, 9, or 10 or more channels. In some implementations, the channels run straight and parallel to each other.

Figure 3:
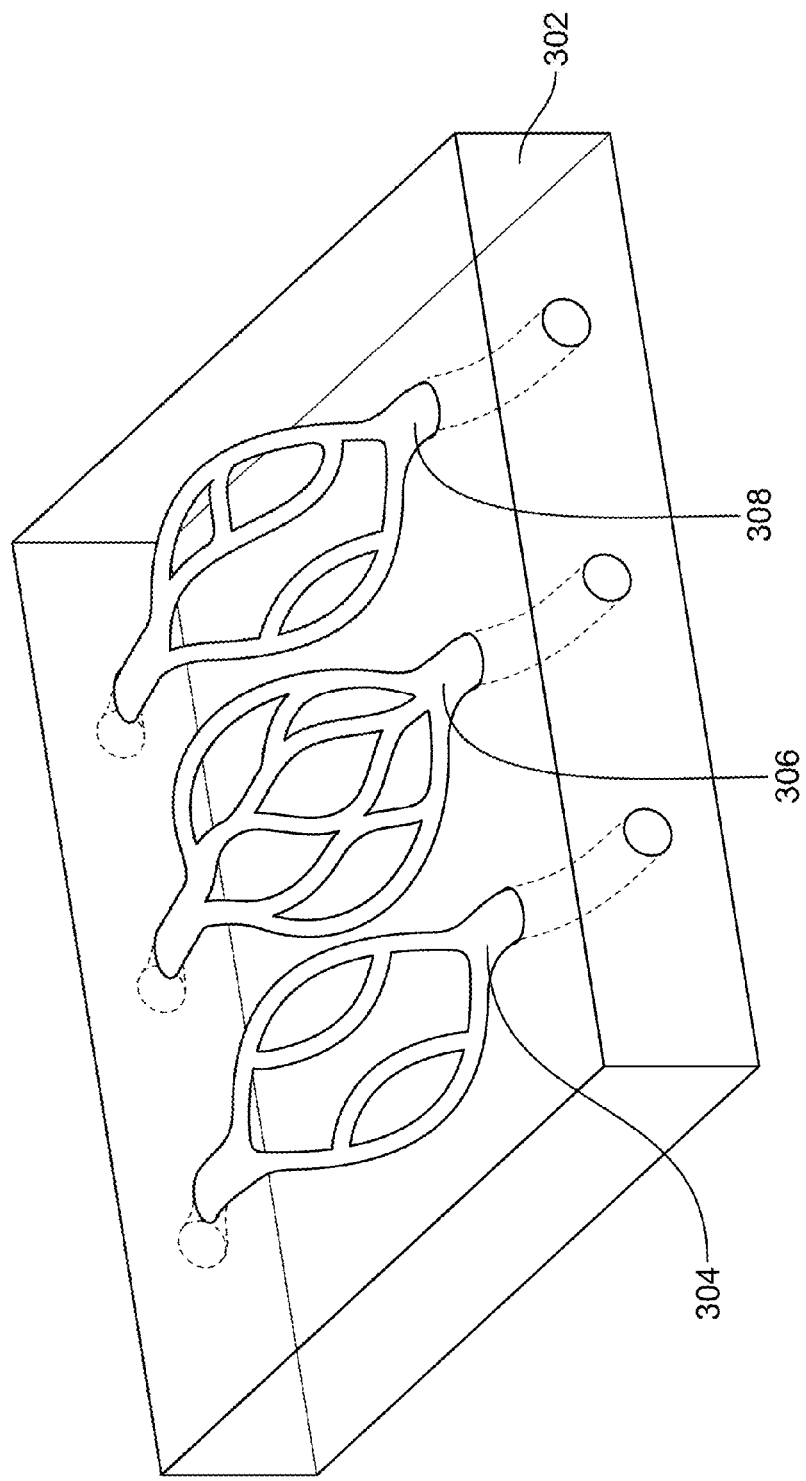
FIG. 3 illustrates a base of an ischemic model device containing channels with capillary-like geometry; according to one implementation of the disclosure.

However, in other implementations the channels are not straight. They can be designed with branching structures that mimic the capillaries that supply the brain with oxygen. An example is shown in FIG. 3. The base 302 includes three channels 304, 306, and 308 that mimic the shape of capillaries. The channels can have varying heights and depths. Capillary-like structures may be produced, for example, as described in Borenstein J et al. "Microfabrication Technology for Vascularized Tissue Engineering", Biomedical Microdevices 4(3) 167-175 (2002). Briefly, photolithographic techniques, injection molding, direct micromachining, deep RIE etching, hot embossing, or any combinations thereof can be used to pattern the above described polymers. The pattern can then be micromachined, for instance by silicon etching or a thick photoresist process. The micromachined wafers may be used as molds to produce scaffolds with a feature resolution of about 1 micron. One appropriate material for the scaffolds is polydimethylsiloxane (PDMS). Additional methods for producing vasculature-like structures are described in US Patent Pub. No. 2007/0148139.

The barrier need not be flat. By recreating some of the structural architecture of the brain, the cells populating the system will inherently be exposed to a more physiological environment. High aspect ratio structures modeling the capillaries that oxygenate the brain can be fabricated using standard fabrication and soft-lithographic techniques. Modified replication techniques can be utilized to transfer these structures into a porous barrier material.

In some implementations, the porous barrier includes a matrix such as Matrigel, collagen, hyaluronic-acid based gel, or agarose. A matrix may promote formation of a three-dimensional cell culture.

Many of the devices described herein comprise fluid-filled channels that are separated from the cell culture chamber. However, other designs are possible. In some implementations, a device includes a single cell culture chamber which has inlets and outlets that allow a direct, laminar flow perfusion of differently oxygenated media through the chamber. For instance, the cell culture chamber may have two inlets and two outlets. One inlet may introduce oxygen-rich media into a first area of the chamber, and the other inlet may introduce oxygen-poor media into a second area of the chamber. Media flows through the chamber fast enough to keep the oxygenated medium from coming to equilibrium with the deoxygenated medium.

II. Cell Components of the Ischemic Stroke Model

The devices herein can be used to model ischemic stroke conditions. Thus, in some implementations, the devices contain CNS cells. In simpler implementations, the device contains a monoculture of a single cell type, for instance neurons. In more complex implementations, the device contains a mixture of CNS cell types. For instance, the culture may contain neurons, astrocytes, and microglia. In some implementations, the culture contains neurons and at least one type of glial cell. The glia may be microglia or macroglia. Macroglial cells include astrocytes, oligodendrocytes, ependymal cells, and radial glia. In some implementations, the cells are neural precursors.

A user may control the ratio of different cell types in the device by selecting an appropriate cell culture medium and by controlling the types of cells introduced into the device. In some implementations, the cell ratios mimic that in the human brain or a rodent brain. In some preferred implementations, the ratio of neurons to glia is about 3:7 which is typical of the human brain. In some implementations, the ratio of neurons to glia is about 7:3 which is typical of the rat brain.

In some implementations, the cells are mammalian cells, for instance human, rat, or mouse cells.

In some implementations, the cultures achieve high levels of viability prior to the ischemic experiment, for instance over 80%, 90%, 95%, 98%, or 99% of the cultured cells may be viable.

In certain implementations, the device is capable of culturing cells for long periods of time, such as at least 5, 10, 15, 20, 25, or 30 days. In some implementations, the cultured cells exhibit functional characteristics of neural cells, such as being GABAergic and glutamatergic.

In certain implementations, the device models one or more characteristics of the core and the penumbral region. In vivo, it is thought that neural cell death takes place in the core soon after the ischemic event, but occurs at delayed time points at the penumbra. The core typically displays enhanced neuro-excitability and loss of membrane potential regulation, which lead to neuronal death. In the core region of the ischemic insult, cells undergo anoxic depolarization and spreading depression, and the dying neurons may never repolarize. In penumbral regions, depolarizations are also observed. However, these peri-infarct depolarizations are generally not sustained and the repolarization of neurons in the penumbra places further metabolic stress on cells in this region. There is some evidence from human studies that these peri-infarct depolarizations continue to occur 48-72 hr following brain injury. In vivo, a direct correlation has been observed between the number of peri-infarct depolarizations and infarct size. Another characteristic of ischemic neural tissue is the ubiquitous second messenger, $Ca^{2+}$, which appears to be a point of convergence for various signaling pathways that result in cytotoxicity after stroke. In addition to promoting further membrane dysfunction, $Ca^{2+}$ overload contributes to nitrosative and oxidative stress in cells by increasing the activity of nitric oxide synthase and triggering mitochondrial damage and concomitant production of nitrous oxide (NO) and reactive oxygen species (ROS). The penumbra may also display elevated apoptosis pathways. Thus, in some implementations, the ischemic model device is used to produce neural cells showing (for example) abnormal membrane potential regulation, calcium signaling, mitochondrial function, NO levels, or ROS levels.

In allowing a user to subject different cells within a single culture to different oxygen levels, the devices herein allow a user to model several important processes. For instance, a user can study the interactions between cells subjected to different oxygen levels. Different populations of cells may interact when, for example, one population secretes a factor that acts on the other population, or when depolarizations in one population promote an energy imbalance in the other population. In certain implementations, the porous barrier separating the channels from the cell culture chamber prevents the wash-out of soluble factors that mediate cross talk between normal, apoptotic, and necrotic cells observed in the penumbral region. Furthermore, in some implementations, the ischemic models herein model the transient peri-infarct depolarizations believed to occur in the penumbra. In addition, in certain implementations, the models herein allow a user to create significant $pO_2$ and glucose gradients observed in the penumbra.

The CNS cells described above model the brain tissue that is affected by ischemic stroke. Other cell types can be introduced into the device to provide a more complex model.

One such cell type is endothelial. Under proper co-culturing conditions, neural and endothelial cells communicate with each other giving rise to what is known as a "neurovascular unit," a functional component of neural tissue in vivo. Thus, to model a vascular unit, endothelial cells can be introduced into the channels. The endothelial cells will adhere to the channel walls and regulate the passage of oxygen, small molecules, and macromolecules into the cell culture chamber. A cross-section of such a device is illustrated in FIG. 4A.

Figure 4A:
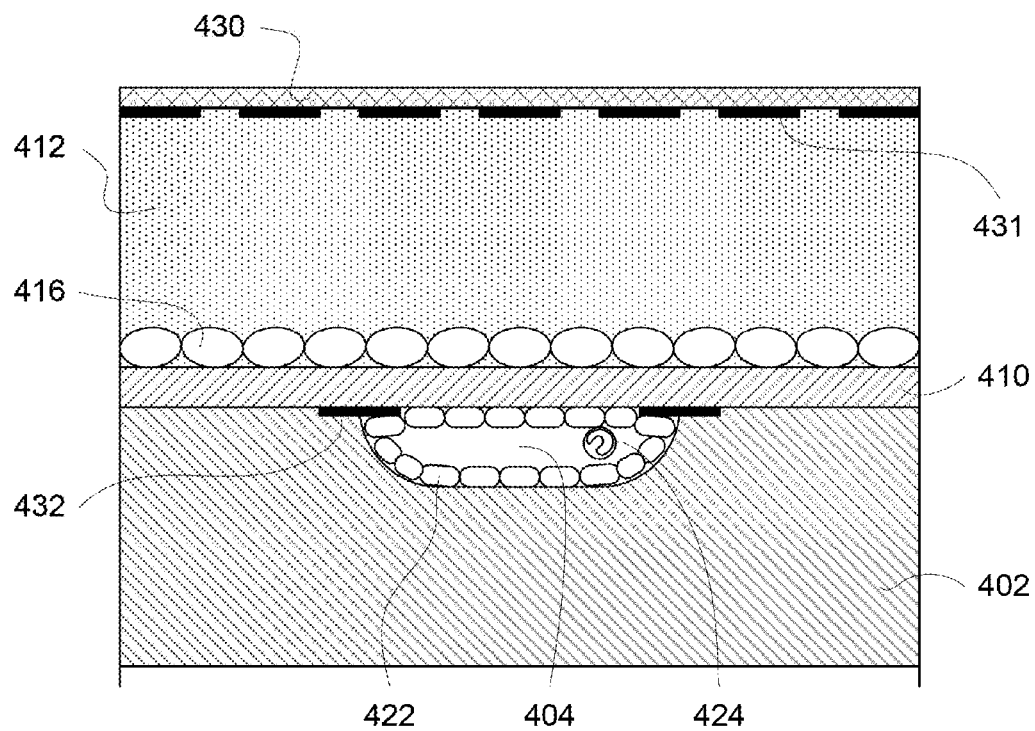
FIG. 4A is a side view of an ischemic model device including CNS cells in the cell culture chamber and endothelial cells and an immune cell in the channel; according to one implementation of the disclosure.

In FIG. 4A, the device 400 includes a base 402 through which a channel 404 runs. The channel is lined with endothelial cells 422. A porous barrier 410 separates the base 402 from the cell culture chamber 412. A layer of CNS cells 416 lies on top of the barrier 410. The endothelial cells 422 can block or actively transport substances from the channel 404 into the cell culture chamber 412.

The endothelial cells 422 can be primary cells or established lines. In some implementations, the cells are immortalized. In some implementations, the endothelial cells form tight junctions. Tight junctions are proteinaceous connections between adjacent cells, forming a barrier that is substantially impermeable to fluid. In tight junctions, the membranes of adjacent cells are sealed together by multiple redundant strands of transmembrane proteins, primarily claudins and occludins. Tight junctions form naturally several contexts including the blood-brain barrier. Examples of appropriate endothelial cells include HUVECs (human umbilical vein endothelial cells). Brain capillary endothelial cell lines are also described in, for example, Hosoya et al. ("Conditionally Immortalized Brain Capillary Endothelial Cell Lines Established from a Transgenic Mouse Harboring Temperature-Sensitive Simian Virus 40 Large T-Antigen Gene" AAPS PharmSci. 2000; 2 (3): article 27) and Fasler-Kan et al. ("Cytokine signaling in the human brain capillary endothelial cell line hCMEC/D3" Brain Res. 2010 Oct. 1;1354:15-22). In certain implementations, the device is seeded with endothelial progenitor cells, which are then allowed or induced to differentiate into mature endothelial cells. Exemplary endothelial progenitor cells (EPCs) are described in von Ballmoos M et al., "Endothelial Progenitor Cells Induce a Phenotype Shift in Differentiated Endothelial Cells towards PDGF/PDGFRβ Axis-Mediated Angiogenesis", PLoS ONE 5(11): e14107.

In certain implementations, muscle cells are also introduced into the models described herein. In some sites (including proximal portions of metarterioles), blood vessels are flanked by smooth muscle cells that regulate blood flow through the capillary. At the transition between metarterioles and true capillaries, annular smooth muscle called a precapillary sphincter typically regulates blood flow into the capillary. Muscle cells can modulate capillary blood flow by contracting or relaxing and by secreting factors such as extracellular matrix, prostaglandins, and cytokines.

A third type of cell that can be introduced into the models herein is an immune cell 424. Immune cells 424 are a relevant part of an ischemic stroke model because they often migrate to the brain following ischemic injury. During an ischemic event, inflammation within the brain and the blood vessels contributes to an ischemic injury. Secretion of inflammatory cytokines directly attracts immune cells. In addition, although the blood-brain barrier usually protects the brain from peripheral immune cells, ischemic stroke can disrupt the blood-brain barrier and impair the integrity of the vascular units that provide oxygen to the brain. These events afford peripheral immune cells (such as peripheral leukocytes and macrophages) entry into the brain. Certain immune cells may cause damage by improperly attacking neural cells, and certain immune cells may promote recovery by clearing necrotic cells. Thus, inclusion of immune cells in the device allows a user to model CNS damage and recovery resulting from immune cells entering the neural tissue.

In some implementations, the cells are chosen to mimic healthy tissue. In other implementations, the cells are selected as a model for a disease or a condition that exacerbates stroke. In some implementations, the cells comprise a mutation that increases the likelihood of a stroke (or a related condition) or the likelihood of serious injury once a stroke occurs. Numerous disorders and mutations predisposing an individual to a stroke are described in Szolnoki "Evaluation of the Interactions of Common Genetic Mutations in Stroke" Methods in Molecular Medicine, 2005, Volume 113, III, 241-249, DOI: 10.1385/1-59259-836-6:241. In other implementations, the cells are modified ex vivo to show such a disease phenotype. For instance, the cells may be treated with a toxin, subjected to RNA interference, or genetically modified to overexpress or underexpress a gene of interest.

The device 400, in certain implementations, includes a first and second layer of electrodes, 432 and 430 respectively. The first layer of electrodes 432 is countersunk into the base layer 402 such that the top of the electrodes 432 do not raise above the top of the base layer 402. The top layer of electrodes 430 are deposited directly onto the under side of the roof of the chamber 412. In certain implementations, the roof 430 is a coverslip that is applied to the device 400 once the cells a fully seeded into the device 400. The electrodes are between about 100 μm and 150 μm in diameter. In certain implementations, the electrodes are stainless steel, platinum, chromium-gold alloys, or silver-silver chloride electrodes. In some implementations, each of the electrodes can act independently as a stimulation and/or recording site, such that a trans-endothelial resistance profile can be created along the path of the channel. In other implementations, the electrodes of a particular layer are electrically coupled to one another, such that a single trans-endothelial resistance is recorded for each channel. In some implementations, the electrodes are used to record local field potentials or other electrical activity. Trans-endothelial electrical resistance can be used as a measure of the integrity and/or health of the CNS cells 416. For example, the above described TER module 170 may induce an electrical pulse in the first layer of electrodes 432. Concurrently, the TER module 170 can record the resulting current response at the second layer of electrodes 430. The TER module 170 then integrates the resulting current response to determine the impedance of the cell layer. In yet other implementations, the electrodes are configured as recording and/or stimulating electrodes.

Figure 4B:
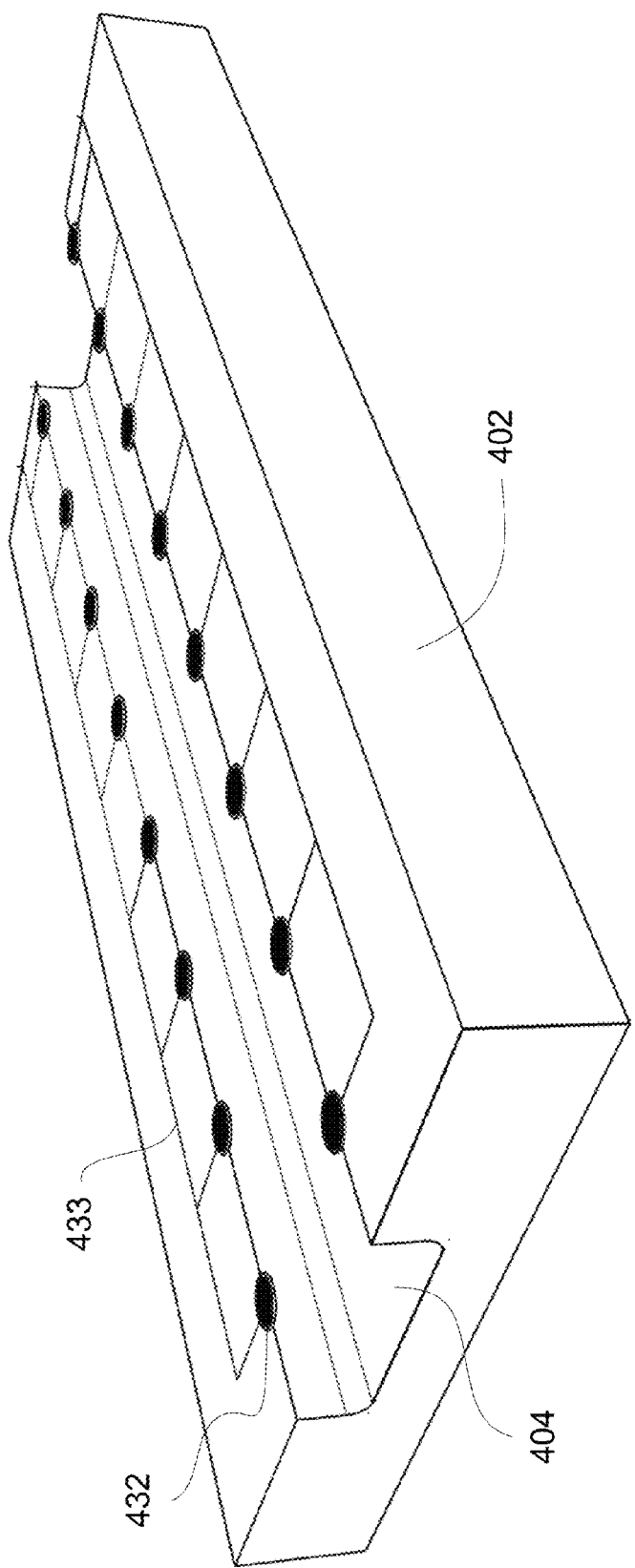
FIG. 4B is an isometric view of the base layer of an ischemic model device; according to one implementation of the disclosure.

FIG. 4B is an isometric view of the bottom layer 402 of device 400. Bottom layer 402 includes a plurality of electrodes 432 which partially overhang channel 404. As illustrates, the electrical leads of electrodes 432 converge onto a single trace 433. As discussed above, in some implementations, the electrodes do not converge onto a single trace 433 such that the electrodes can be independently accessed.

III. Methods of Using the Ischemic Stroke Model

Figure 5:
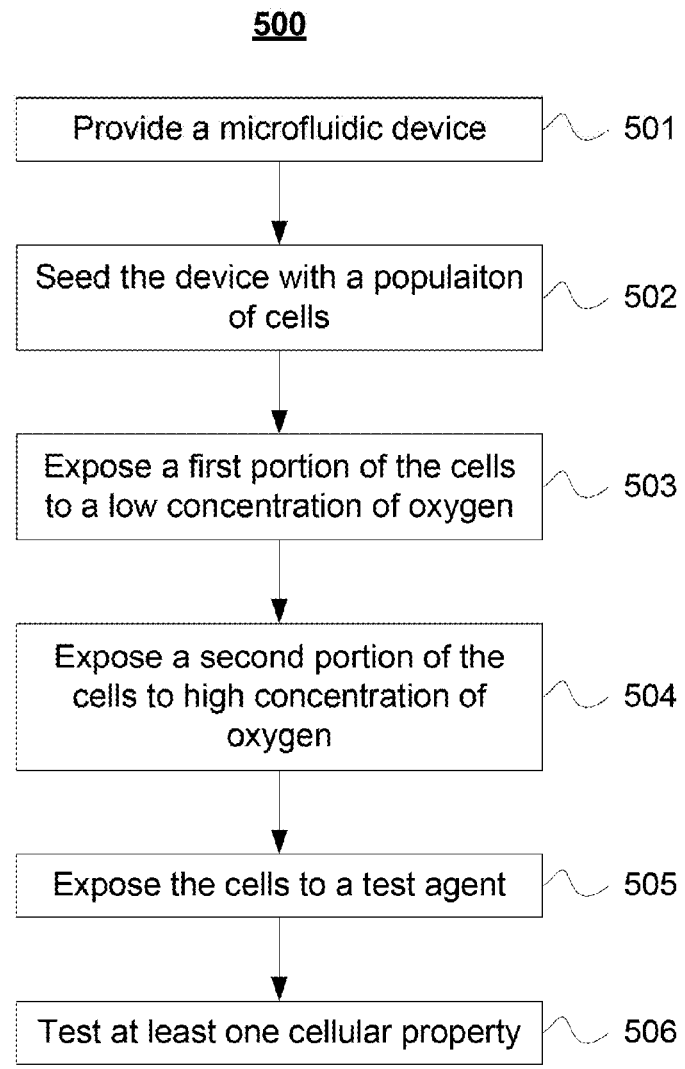
FIG. 5 is a flow chart of a method for modeling ischemic stroke using a system similar to the system of FIG. 1; according to one implementation of the disclosure.

FIG. 5 is a flow chart illustrating a method 500 for modeling ischemic stroke. Further method examples are provided in Sections III (A), (B), (C), and (D), but briefly, the method of modeling ischemic stroke begins by providing a microfluidic flow device (step 501). A population of cells is then seeded into the microfluidic flow device (step 502). A first portion of the population of cells is exposed to a low concentration of oxygen (step 503) and a second portion of the population of cells is exposed a high concentration of oxygen (step 504). The population of cells are then exposed to a test agent (step 505). Finally, at least one cellular property is measured (step 506).

As set forth above, and referring to FIGS. 1B, a microfluidic flow device is provided (step 501). As discussed above, the microfluidic flow device can be a single or multi-channel flow device. The at least one channel of the microfluidic flow device is separated from a cellular chamber by a porous membrane. In some implementations, the porous membrane is configured such that the cells in the cellular chamber do not experience a shear force as fluid flows through the at least one channel. In some implementations, the cellular chamber is sealed to reduce the cells exposure to oxygen or other gasses.

Next, a population of cells is seeded into the microfluidic flow device (step 502). In some implementations, the cells are from the central nervous system, and can include such cells as neurons, microglia, astrocytes, oligodendrocytes, or neural progenitors. In certain implementations, the cells are dissociated neural cells and in other implementations the cells comprise an acute brain slice.

The first portion of the cells is exposed to low concentrations of oxygen (step 503) while a second portion of cells is exposed to higher concentrations of oxygen (step 504). As described above, the there are a number of ways to create an oxygen gradient across the cells in the microfluidic flow device. For example, an increase in oxygen concentration proximal to the channel can be created by flowing oxygen rich fluid through the flow channel. Alternatively, a decrease in oxygen concentration proximal to the channel can be created by flowing oxygen scavengers through the flow channel. The oxygen gradient is designed such that the lack of oxygen creates an ischemic state within the first portion of cells. In some implementations, the fluid in the cellular well can be augmented with oxygen or oxygen scavengers. In certain implementations, there is a third portion of the cellular population located with the region of the cellular well that transitions from low to high oxygen concentrations. In some implementations, the microfluidic flow device is placed into an atmospheric control system, such as the ACS 120, which further controls the amount of oxygen to which the cells are exposed.

As described below in relation to FIG. 6, the cells are exposed to a test agent (step 505). In some implementations, the test agent is a chemical therapeutic that promotes neural cell survival, inhibits neurodegeneration, inhibits necrosis, or inhibits apoptosis. In other implementations, the test agent may be high concentrations of oxygen, cells (e.g., stem cells), or electrical stimulation.

Next, at least one cellular factor is tested (step 506). Different factors can be tested in relation to different biochemical studies, microscopy studies, and drug screening studies. For example, in some implementations, the testing step may include testing for a specific chemical secreted by the cells during experimentation, measuring trans-endothelial electrical resistance, measuring cellular fluorescence, or any combination thereof. Below, several examples are provided to further illustrate modeling ischemic stroke with the above described microfluidic device.

A. Biochemical Studies

The ischemic stroke model devices herein may be used to study the biochemistry of ischemic regions. To that end, the model allows a user to collect samples of cells or fluid that has contacted the cells. In some implementations, a user takes a sample of cells from a region modeling the core and/or penumbra, and compares them to cells from a region modeling normoxic tissue.

In other implementations, a user can withdraw an aliquot of fluid from the cell culture chamber. This aliquot can be tested for the presence of factors secreted by the cells.

In still other implementations, the user withdraws a sample from effluent from a channel. Because the barrier is porous, it is expected that factors secreted by the cells will enter the channels. Sampling effluent from the channels has the advantage of not disturbing the tissue culture chamber. Thus, the device permits dynamic sampling of perfusates or effluents from discrete areas in the culture. These samples can be tested for the presence of (for example) neurotransmitters and cytokines.

The device can also be used to observe the cells' response to an exogenous substance. The exogenous substance can be added to the cell culture chamber or one or more of the channels. For instance, in some implementations, cytokines are added to stimulate the inflammation that can accompany ischemic stroke in vivo. Appropriate cytokines for this purpose include TNF-a and IL-1β.

B. Microscopy

The ischemic model can be designed to permit microscopy of the cultured cells. Monitoring the cells by microscopy allows long-term, non-invasive analysis of stroke progression over a physiologically relevant time course. If the device is sufficiently transparent, it can be placed on a microscope stage and inspected using light microscopy. Generally, the base, barrier, and cell culture medium should be sufficiently transparent to allow light to pass through the portions of the device where the cells are cultured. PDMS is one optically transparent material. In some implementations, the device allows at least 90%, 95%, 98%, or 99% of light of a given wavelength to pass through components of the device disposed along a path that is perpendicular to the porous barrier and that passes through the cells.

Fluorescence microscopy may also be used. Numerous relevant fluorescent dyes are available for monitoring, e.g., membrane potential, pH, and free $Ca^{2+}$ levels. In addition, the localization and/or levels of specific enzymes can be monitored using fluorescent fusion proteins. In some implementations, multiple analytes are detected at once using fluorophores with compatible emission and excitation spectra.

To be suitable for fluorescence microscopy, the device should be sufficiently transparent and have little or no fluorescence when illuminate with at least one wavelength. In some implementations, the device is substantially non-fluorescent in response to far-red, red, orange, yellow, green, blue, violet, or ultraviolet light. If the cell culture chamber is sealed, it may be sealed using glass which is UV compatible and permits quantitative fluorimetry.

The slimness of the entire device can be attuned to be compatible with high resolution imaging for high content analysis. In some implementations, the microchannel thickness can be varied (using spin coated and alaminated layer of PDMS) from 100 μm-2 mm, a large spectrum that can facilitate high resolution microscopy for high content analysis.

C. Drug Screening

One major use for the devices herein is screening therapeutics. The therapeutic may be, for instance, a small molecule, a macromolecule, or a cell-based therapeutic such as a stem cell or an immune cell. The therapeutic may be, for instance, an agent that promotes neural cell survival, inhibits neurodegeneration, inhibits necrosis, or inhibits apoptosis.

The test therapeutic may be added directly to the cell culture chamber or to one or more of the channels. In some implementations, the therapeutic is a cell and it is added to the channel so that it must traverse the porous barrier before reaching the neural cells. In some implementations, the channels comprise a layer of endothelial cells, and the therapeutic must traverse the endothelial cells before reaching the neural cells.

Drug screening is often performed in a high-throughput manner, and the devices herein are amenable to high-throughput screening. FIG. 6 illustrates three devices 626, 628, and 630 arranged in parallel. Each device has three channels so that each device can apply three different solutions to different regions of cells. Three sets of tubing 632, 634, and 636 link the channels to three peristaltic pumps 638, 640, and 542. Each of the devices in FIG. 6 could contain a different test agent. In some implementations, a device contains no test agent or it contains a control agent with a known effect. In some implementations, the peristaltic pumps deliver test agents to the cells via the channels. For simplicity, FIG. 6 only depicts three devices; however, the number could readily be scaled up.

Figure 6:
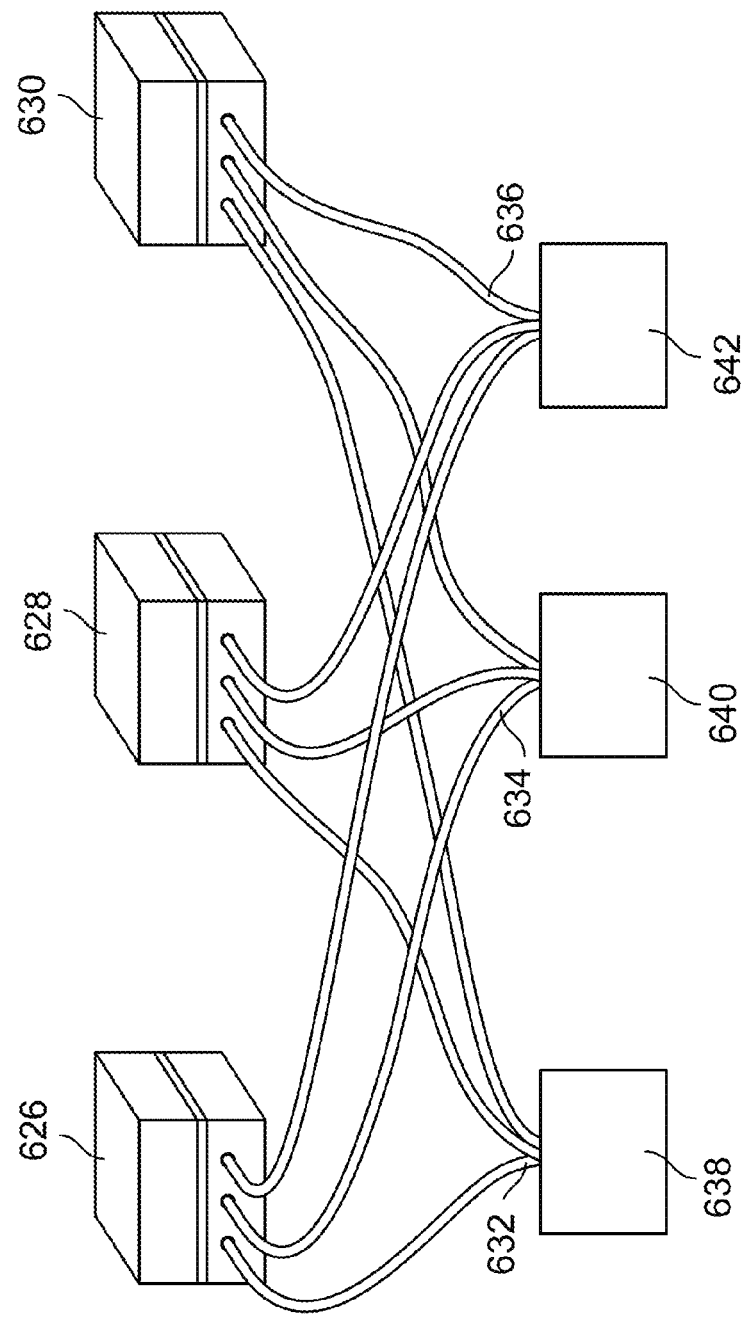
FIG. 6 illustrates three ischemic model devices arranged in parallel; according to one implementation of the disclosure.

In contrast to FIG. 6 which arranges the devices in parallel, the devices could be arranged in series such that fluid flows through a channel in one device and then into a channel in the next device and so on. Such a setup can be arranged so that every device in the series receives substantially the same concentration of oxygen or other factor from the channels. To accomplish this uniformity, the channels should be sufficiently large and the concentration of oxygen or other factor in the channel should be sufficiently high that it is not exhausted by the time it reaches the final device in the series.

D. Uses for Modeling Conditions other than Ischemic Stroke

The devices herein, though often referred to as ischemic stroke models, can also be used to model other conditions in which two or more nearby populations of cells, e.g., populations along a diffusion gradient, are exposed to different environments. In certain implementations, the devices are used to model the communication or interaction between the two or more populations of cells through, e.g., diffusible signals.

First, the devices can be used to model neuronal injury. Typical sources of neuronal injury include chemical toxicity, neurodegenerative diseases such as multiple sclerosis and Amyotrophic lateral sclerosis, angiogenesis (for instance when triggered by stroke), and certain forms of metastasis in which cancer cells invade the CNS. In some implementations, the agent that induces the injury is introduced into the chamber, and in some implementations, the agent is introduced into one or more channels.

Second, the devices can be used to model ischemia or hypoxia in non-neuronal cell types. For instance, solid tumors are often hypoxic and this model can replicate the hypoxic condition. The devices can also be used to model ischemia in cardiac muscle tissue.

Third, the devices can be used to model basic neuronal cell functions. For instance, they can be used to model axonal guidance for central and peripheral nervous system regeneration research. The devices can also be used to study cell migration during development and stem cell biology and cell invasion during wound healing and inflammatory conditions.

Fourth, the devices can be used to model numerous infectious diseases that affect the brain. Examples include HIV, bacterial meningitis, cerebral malaria, prion diseases, Ebola, hantavirus, and hemorrhagic fevers.

Fifth, the devices can be used to model cell therapies. Following an injury (for example, a neuronal injury as described above), a user could introduce a test cell into the device to determine the test cell's effect on the injured cells. For instance, the user could model the test cells' effect on the blood-brain-barrier and/or neural repair (neurogenesis). In some implementations, the test cell is a stem cell, a cord blood cell, or a progenitor cell. In some implementations, the test cell is administered to the fluid-containing chamber, and in some implementations, the test cell is administered into one or more channels.

Sixth, a user can study "bystander effects" using the devices herein. The bystander effect is a phenomenon in which a therapeutically administered cell affects nearby endogenous cells, for instance by secreting factors such as growth factors or by taking in factors from the cellular milieux. In some implementations, the therapeutic cell promotes neuronal repair. In some implementations, the therapeutic cell (such as a stem cell, a progenitor cell, or myeloid cell) drives out amyloid beta from the neural side to the vascular side.

IV. Kits

In some implementations, the device is provided as a kit that a user can assemble. The kit may include (a) a chamber wall capable of delineating a cell culture chamber that contains tissue culture cells and medium, (b) a base comprising a channel, wherein the channel has an inlet and an outlet, and the channel is sized to be proximal to a first region of the chamber and distal from a second region of the chamber; (c) a microporous membrane suitable as a substrate for cell culture, wherein the microporous membrane is sized to separate the channel from the chamber. The kit may also include means for securing the microporous membrane between the chamber and the channel. The means for securing the microporous membrane between the chamber and the channel may be, for instance, one or more of: adhesive, screws, clamps, a waterproof sealant, and an interlocking assembly such as a raised portion that fits securely into a cavity.

EXAMPLES

I. Fabrication of a Microfluidic Cell Culture Device

A microfluidic device for subjecting different neural cells to different environments can be produced according to the methods below. This device bears a neural compartment juxtaposed above three parallel microchannels. The neural compartment is separated from the microchannels by a microporous polyester membrane bonded irreversibly through a thin layer of silicone adhesive. FIG. 1 shows an exploded view of such a device.

The neural chamber accommodates a cell culture area of ~0.5 cm$^2$, close to the surface area of a section of adult rat brain. The channels are fabricated to have dimensions of 1 mm width, 250 µm height and 1.1 cm (length) separated from each other by 1 mm. The design of the neural chamber facilitates standard well-plate format of cell culture, which is simple, routine, and does not require continuous perfusion. The reservoir in the culture chamber holds ~150 µl media. The membrane (10 µm thickness and pore size 8 µm) in between the neural chamber and the microchannels acts as an efficient mechanical barrier to prevent direct exposure of shear to neural cells and washing out of necessary factors (a significant advantage over focal injury model). The sides of the device can be sealed with silicone glue or epoxy to minimize $O_2$ diffusion from bulk (as PDMS is permeable to oxygen). Prior to a hypoxic experiment, the cell culture media in the neural chamber may be replaced by physiological saline solution (PSS) and sealed using a glass coverslip to limit $O_2$ diffusion from ambient environment. PSS generally contains 140 mM NaCl, 1.2 mM $MgCl_2$, 3 mM KCl, 2.5 mM $CaCl_2$, 7.7 mM glucose, and 10 mM HEPES, and is set to a pH of 7.4 with NaOH.

Figure 7:
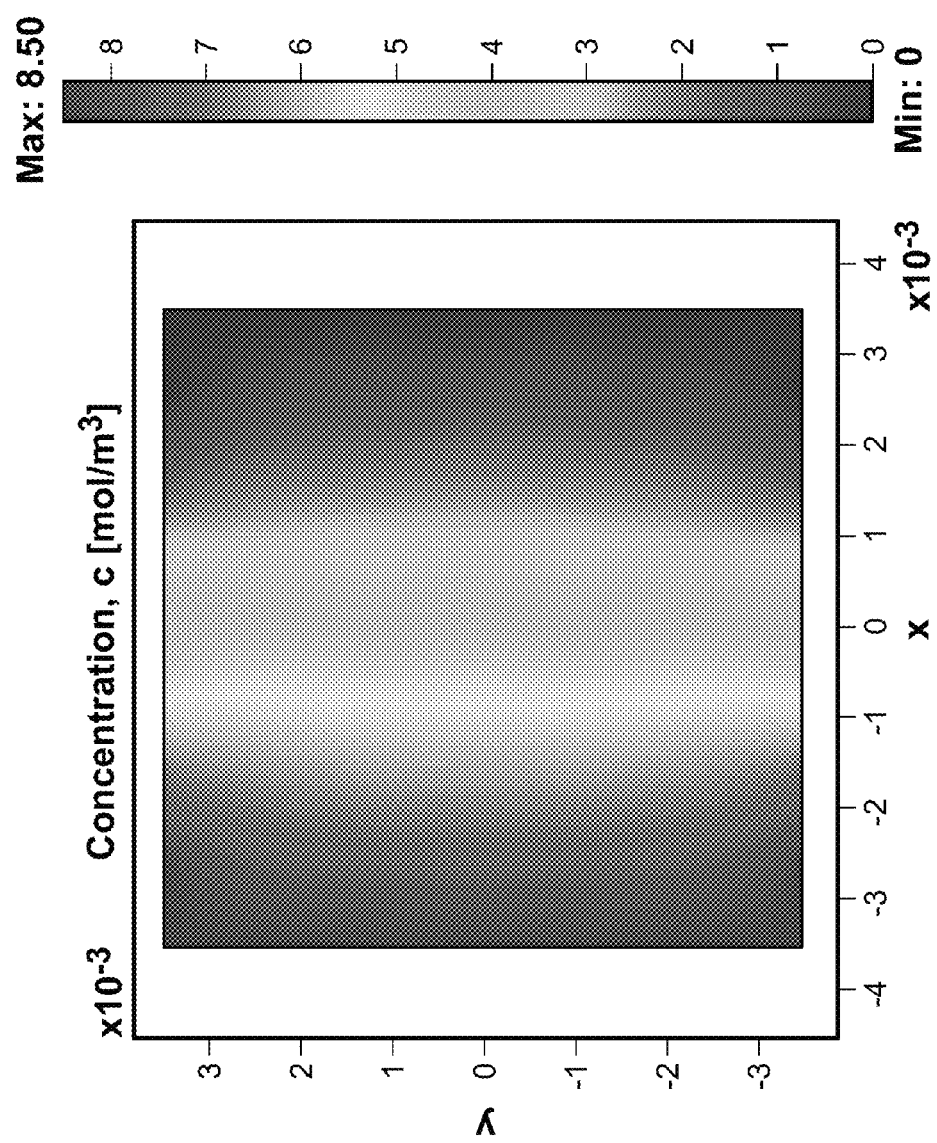
FIG. 7 illustrates a suitable oxygen gradient for the ischemic model device. The x and y labels refer to the coordinates of the device in meters.

The flow of separately oxygenated media at optimized flow rates (in a sealed device) were modeled computationally using COMSOL Multiphysics™ software chemical engineering module (FIG. 7). The computation models the steady state levels of oxygen in the device, without oxygen consumption.

Figure 8:
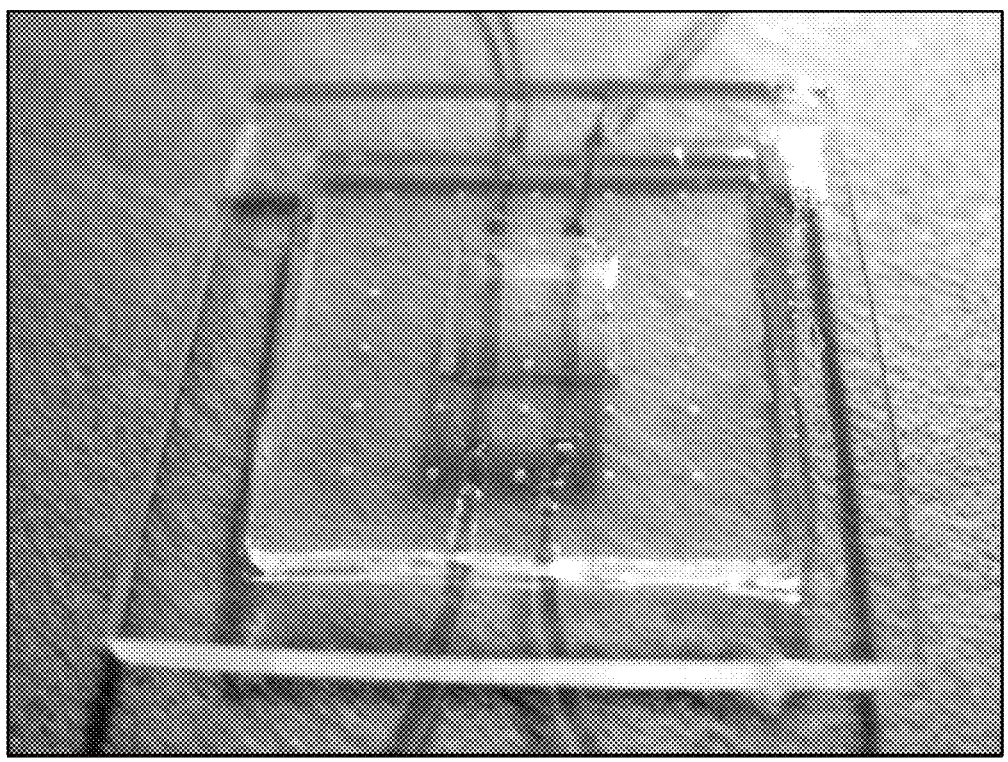
FIG. 8 is as photograph of an ischemic stroke model device with two channels.

II. Use of a Microfluidic Device for Studying the Effects of an Ion Gradient on Neural Cells A microfluidic device was fabricated. This device had a neural chamber juxtaposed above two parallel microchannels of dimensions 1 cm (length)×800 µm (width)×and 100 µm height. The channel layer was fabricated using soft lithographic molds and cast with PDMS pre-polymer. The neural chamber was a molded block of PDMS polymer punched out to accommodate a cell culture area of ~0.35 cm$^2$. A microporous polycarbonate (PC) membrane with 10 µm pores separates the chamber from the microchannels. The two casted layers were bonded to the PC membrane using a thin uniform layer of silicone glue (3140, Dow). FIG. 8 is a photograph of the device where one channel is filled with green dye and the other with orange dye.

Following device assembly, the chips were sterilized with ethylene oxide and the neural chamber was coated with poly-D-lysine (50 µ/ml) overnight at 37° C. Rat cortical neural cells isolated from embryonic day 18 Sprague-Dawley pups were then seeded into the neural chamber at a density of 105 cells/cm$^2$. Methods for culturing neurons derived from rat embryos are described in Katnik et al. ("Sigma-1 Receptor Activation Prevents Intracellular Calcium Dysregulation in Cortical Neurons during in Vitro Ischemia" J Pharmacol Exp Ther. 2006 December; 319(3):1355-65). The cells were differentiated into a predominant mixture of neurons, astrocytes, and microglia following 10 days of culture in Neurobasal™ medium supplemented with 2 mM L-glutamine, 10% v/v fetal bovine serum, serum free B27, 10 ng/mL basic fibroblast growth factor (FGF), and 1% v/v penicillin/streptomycin.

Figure 9:
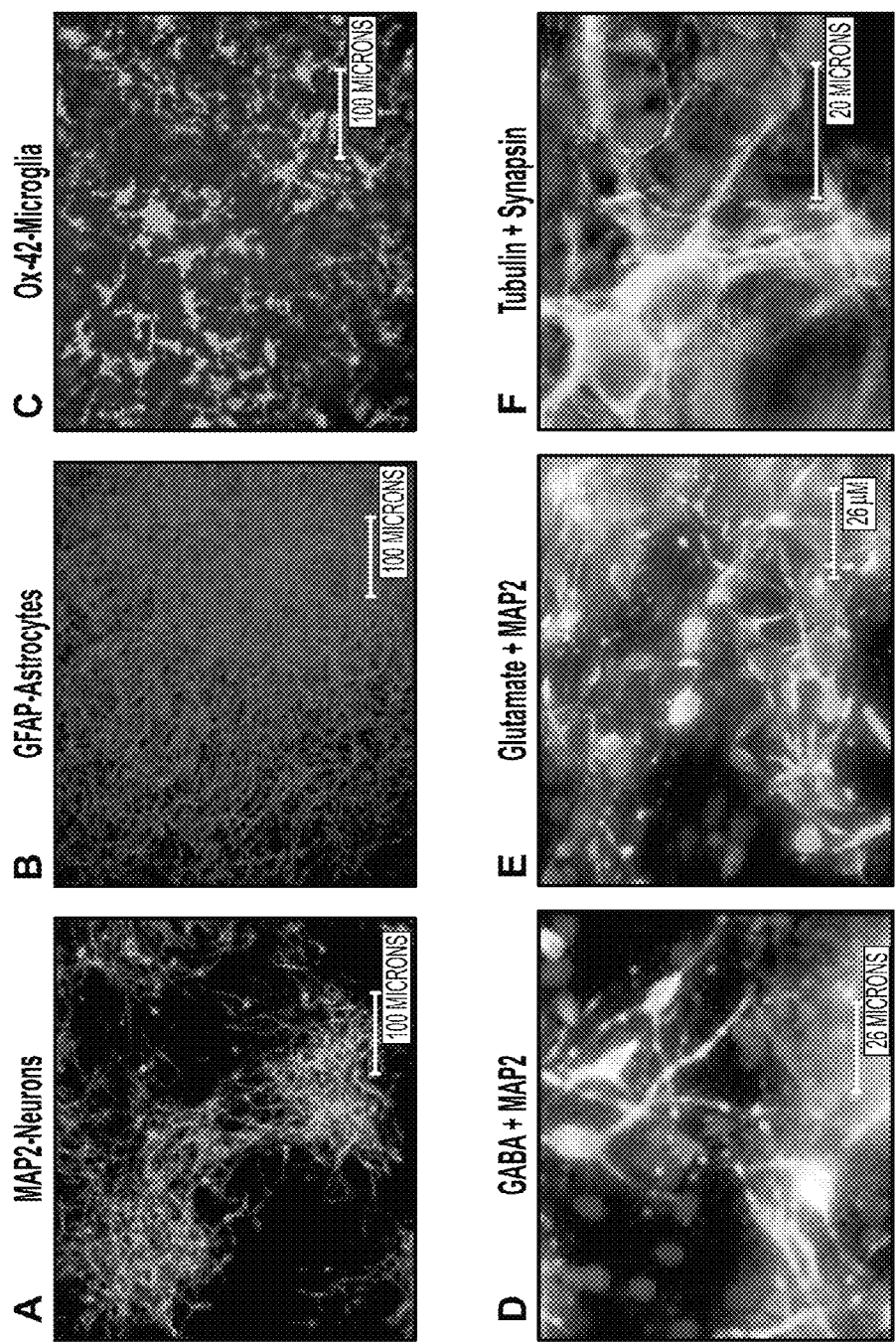
FIGS. 9 A-F illustrates fluorescence microscopy images of neural cells cultured in an ischemic stroke model device.
Figure 10:
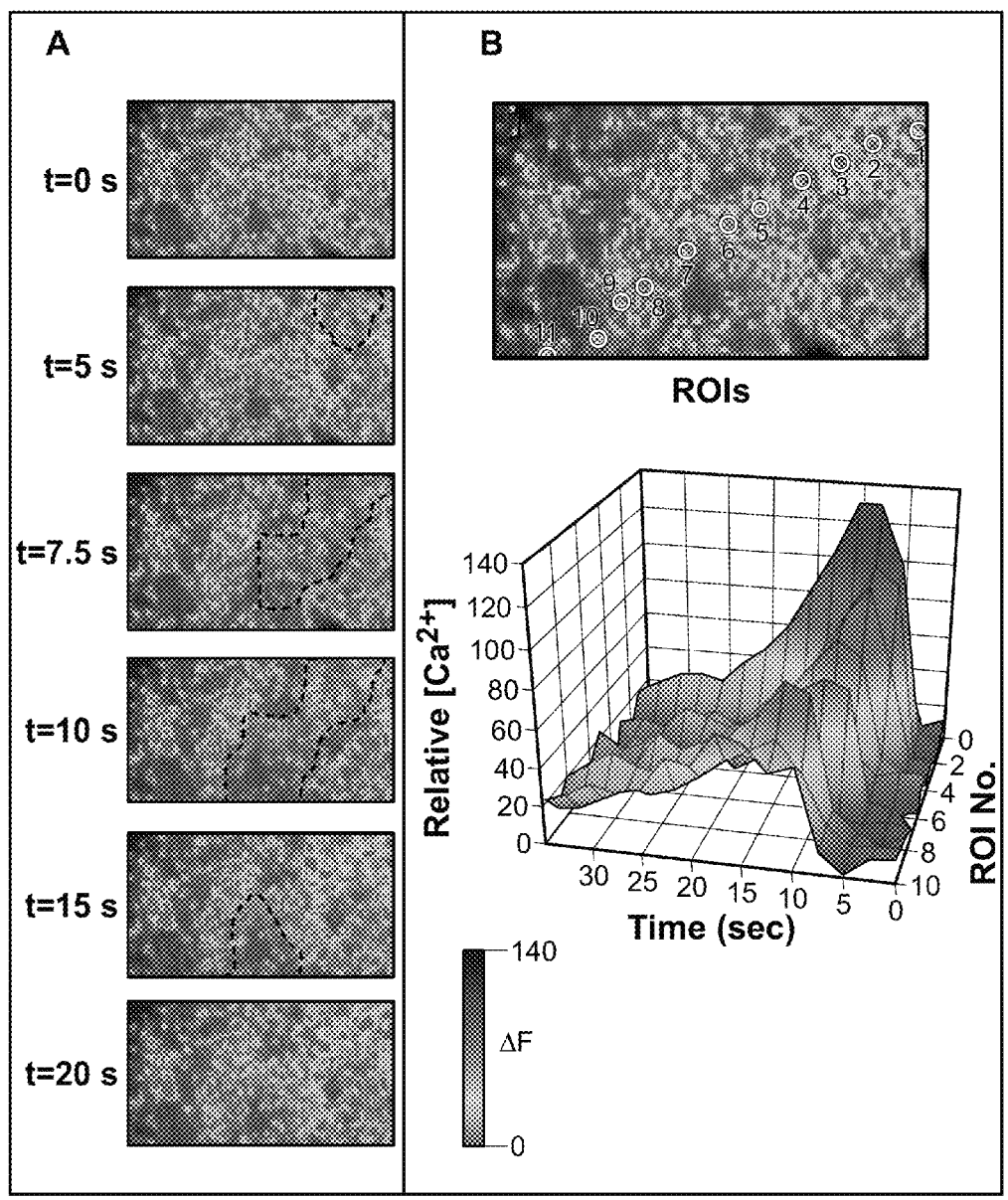
FIGS. 10 A and B depict the calcium levels in neural cells exposed to a potassium gradient. Panel A is a series of images gathered in a time course experiment. The line in the t=20 s panel represents 50 µm. Panel B shows the regions of interest (ROI) mapped onto a photograph of the cell culture (upper panel). The scale on right indicates the change in fluorescence intensity (510 nm, emission; 380 nm, excitation), with higher intensity representing higher $[Ca^{2+}]i$. The relative $[Ca^{2+}]i$ levels at each region of interest over time are graphed in the lower panel with ROI #1 representing the ROI at the upper right and ROI #11 representing the ROI at the lower left.

Immunohistochemical staining provided evidence that the cells had differentiated, and that neuron had formed synaptic contacts and were actively synthesizing neurotransmitters (FIG. 9). The top three panels of FIG. 9 show, from left to right, neuronal cells identified using the marker MAP2, astrocytes identified using the marker GFAP, and microglia identified using the marker Ox-42. The bottom three panels of FIG. 9 are merged images where DNA is shown in blue and immunofluorescence signal is shown in the red and green channels. From left to right, GABA is shown in green and MAP2 is shown in red, glutamate is shown in green and MAP2 is shown in red, and tubulin is shown in green, and synapsin is shown in red. The viability of these cultures exceeded 95% after 10 days. A typical cell-type ratio is 20-30% neurons, 65-80% astrocytes, and 2-5% microglia. Of the microglia, typically more than 75% are resting or ramified.

The neural cells in the microfluidic chamber were studied using $Ca^{2+}$ fluorometry with fura2-AM. Basal levels of $[Ca^{2+}]i$ are represented as red in the image pseudo color, regions of elevated $[Ca^{2+}]i$ are blue. The top of the field of view was oriented along the inside edge of one of the microchannels. Just prior to acquiring the first image the normal physiological saline solution (PSS) flowing through the channel was changed to PSS containing 30 mM $K^+$. Delivery of high $K^+$ via the microchannel triggered a $[Ca^{2+}]i$ wave (area outlined by dashed line in images in FIG. 9A). The change in $[Ca^{2+}]i$ reveals, first, that there is sufficient exchange between the microchannel and the culture compartment to produce a change in $K^+$ and elicit a cellular response. Second, there is decremental conduction of the signal and the effect of high $K^+$ is temporally and spatially limited (FIGS. 9A-B). Third, the model allows a user to effectively record from a broad area of the chip such that responsive and non-responsive areas can be simultaneously monitored. Thus, data obtained with this model suggests that the model can successfully generate a discrete area of ischemia.

III. Establishment of $O_2$ Gradients Using an Ischemic Model Device

The first step in obtaining a simulated core and a penumbral region in the microdevice will be to obtain suitable oxygen gradients in the presence of differentiated neural cells. The level of oxygen in the device can be measured using a glass insulated platinum needle (~30 μm in diameter) connected to a Polarographic Amplifier (A-M Systems Model 1900). A polarization voltage of 20.6 V can be used. At this voltage, the current output is proportional to the concentration of dissolved O2. To enable access to the chamber by the electrode, the coverslip which is otherwise used to seal the chamber can be replaced with a layer of oxygen impermeable paraffin oil.

Oxygen gradients can also be varied by adjusting the following variables. First, the number or dimensions of the channel can be altered. Second, the height (and therefore the volume) of the neural culture can be altered. Third, the flow rate of the solution through the microchannels can be varied. In some implementations, multiple peristaltic pumps are used to provide a different flow rate through different microchannels. Fourth, one can select one or more methods for increasing or decreasing $O_2$ concentration. For instance, one can bubble PSS with $N_2$ to eliminate $O_2$ in the ischemia chamber. As another example, one can add an $O_2$ scavenger to the chamber or a channel. One example of an $O_2$ scavenger is $Na_2SO_3$, which may be used at 500 μM on cultured cells. In some implementations, the device has three channels, and the channel corresponding to the normoxic region contains fluid with 95% oxygen, the channel corresponding to the penumbra region has 5% oxygen, and the channel corresponding to the core has 0% oxygen.

Because an important function of oxygen is promoting glucose metabolism, the effects of hypoxia can be amplified by lowering the levels of glucose to which the cells are exposed. For instance, glucose may be reduced to 2 mM in the PSS for the penumbra channel and to 0 mM in the core channel.

IV. Detecting Apoptosis and Necrosis in Cells Subjected to High or Low Oxygen Levels in an Ischemic Model Device The devices herein allow a user to quantify the number of healthy, apoptotic, and necrotic cells at select locations relative the channels in the device. From the oxygen gradient production condition obtained in Example III, one may utilize a Promokine™ Kit to quantify the distribution of apoptotic, necrotic, and healthy cells in the device. Apoptotic cells can be identified with fluorescein-labeled Annexin V (green). Necrotic cells can be labeled with ethidium homodimer (red). All cells can be counterstained with Hoechst (blue). Following staining, the cells can be fixed with 2% formaldehyde and visualized using filter sets for FITC, rhodamine and DAPI. Cells appearing green (with blue), red (with blue), and blue only can be labeled as apoptotic, necrotic, and healthy, respectively. Five different sections along the length of each microchannel will be manually counted and quantified. Subsequent to quantification, the death rates can be compared with historical animal data from in vivo experiments. The parameters outlined in Experiment III can be used to produce a neural cell culture with necrosis and apoptosis levels typical of core, penumbra, and healthy tissue.

Apoptosis and necrosis can be detected according to the following protocols. One may use the Invitrogen Vybrant Apoptosis Assay Kit #6 or combination of annexin V Alexa Fluor® 350 conjugate and propidium iodide. Both the assay kit and the alternative stain have a fluorescent spectrum compatible with di-8-ANEPPS, fura-2 and DAF-FM and so can be used in combination with these indicators. In this and other experiments, fluorometry data can be compared with apoptosis/necrosis markers using the microchannels and the edge of the chamber as landmarks.

V. Detecting Electrical Activity in Neurons Subjected to High or Low Oxygen Levels in an Ischemic Model Device The devices herein allow a user to study neuron depolarization under ischemic conditions. The voltage-sensitive dye, di-8-ANEPPS, can be used to monitor electrical activity in cell cultures within the microfluidic chamber before and during oxygen-glucose deprivation (OGD) using the parameters set out in Example III to produce the desired normal, penumbra and core regions. Cells can be imaged using a Zeiss Fluar 10×/0.50 objective (23 mm field of view). One may sample at acquisition rates ranging from 0.033 Hz to 1 Hz to determine what is the minimum rate that permits detection of the onset and extent (spatial and temporal) of spreading depression (SD) and peri-infarct depolarizations (PIDs). The higher sampling rate (1 Hz) is sufficient to permits use of fluorescent imaging techniques to record bursts of electrical activity in cortical neuron cultures. However, for extended recordings (>1 hr), lower sampling rates may be preferable to reduce photobleaching of the voltage-sensitive dye. These lower rates will still permit monitoring of long-lived changes in membrane potential, such as those associated with SD and PID. The sampling can be varied within a single experiment to determine how the SD and PID affect bursting behavior. In some experiments one can evoke depolarization within the normal zone by adding high K+ via the microchannel to determine if depolarization of cells in this region affects membrane responses in the penumbra or core. Similarly, the response to reperfusion can be determined.

The voltage sensitive dye di-8-ANEPPS can be used according to the following protocol. Cells can be incubated in 2 μM di-8-ANEPPS (10 mM stock solution in DMSO) for 20 minutes at room temperature. Cells can be illuminated at 450 nm and emission intensity>570 nm can be recorded using SlideBook software. The typical sensitivity of di-8-ANEPPS to membrane potential changes is 1% .F/F for 100 mV.

In this and other fluorometry experiments, the fluorometry data can be analyzed as follows. The data can be converted to text files and imported into Clampfit 9 for analysis. For ROS fluorometry, fluorescence intensity can be analyzed using non-linear or linear regression, as appropriate. The rate of change in fluorescence (.F/min) can be calculated before, during and following each condition. Statistical analysis can be conducted using SigmaPlot 9 and SigmaStat 3. Statistical differences can be determined using paired and unpaired t-tests for within group and between group experiments, respectively, and will be considered significant if $P<0.05$. multiple group comparisons one may use either a 1-way or a 2-way ANOVA, as appropriate. When an ANOVA indicates significant difference, one may use a Tukey Test to determine significance between groups. For all experiments one may conduct a Power analysis with SigmaStat 3.

VI. Studying $Ca^{2+}$ and NO Signaling in Neurons Subjected to High or Low Oxygen Levels in an Ischemic Model Device The devices herein allow a user to study neuronal $Ca^{2+}$ signaling under ischemic conditions. An oxygen gradient can be produced according to Example III. $Ca^{2+}$ levels can be assayed using fura2 as described in Example II. The magnitude and spatial and temporal patterns of $[Ca^{2+}]i$ changes evoked by OGD can be determined. Changes in $[Ca^{2+}]i$ can be compared with the distribution of apoptotic and necrotic cells. By using both di-8-ANEPPS with fura-2, a user can determine the correlation between membrane potential changes and $[Ca^{2+}]i$ dyshomeostasis.

Using parameters for OGD and reperfusion duration according to Example III, neuronal cultures can be subjected to localized ischemia and reperfusion. To detect NO levels, neurons can be loaded with the NO-indicator dye DAF-FM and imaged at 0.033 Hz. Alternatively or in combination, cells can be loaded with DHE imaged at 0.033 Hz to measure ROS production. In addition, cells can be loaded with both fura-2 and DAF-FM. Simultaneous $Ca^{2+}$ and NO fluorometry can be carried out to determine the correlation between changes in the cellular levels of these molecules in response to ischemia. Apoptosis and necrosis can be assayed simultaneously using the Invitrogen Single Channel Annexin V/Dead Cell Apoptosis Kit, which uses fluorescence intensity in the green channel to identify apoptotic and necrotic cells.

To measure the rate of NO and $O_2$-production, cortical neurons can be loaded by incubating for 1 hr at 23° C. in 5 µM DAF-FM or for 10 min at 23° C. in 2 µM DHE (both in PSS, 0.1% DMSO). For DAF-FM and DHE the excitation wavelengths can be 480 nm and 515 nM, respectively, and emission light can be collected at 520 nm and 605 nm, respectively. The same hardware and software used for $Ca^{2+}$ imaging can be used for these experiments. One may monitor both $[Ca^{2+}]i$ and NO by alternating illumination of the sample with excitation of 350, 380, and 490 nm sequentially and collecting emitted light at 510 nM. The sampling rates may be 0.33 Hz, 0.033 Hz for 30 min and 6 hr experiments, respectively.

VII. Studying Neuron-Secreted Factors in an Ischemic Model Device

The devices described herein allow a user to sample effluents from discrete regions of the chamber as well as from the channels. For instance, a user may collect the effluent from each microchannel before, during and after exposure to OGD. The user may then measure the levels of cell-secreted factors (such as IL1 IL10 and TNF-a) in the perfusates collected from normal, penumbral and core regions following disruption of $pO_2$ and glucose delivery. Using the device, one may measure cytokines and specific neuromodulators or neurotransmitters such as glutamate and ATP in the effluent.

The secreted factors may be tested using a variety of assays such as ELISA, Western blot, capillary zone electrophoresis (CZE) or electrochemiluminiscence. If the ELISA assay is used, collected effluent can be centrifuged for 10 minutes at 1200 g followed by 0.2 µm filtration to remove particulate matter. Solutions can be analyzed for the presence of cytokines using ELISA Assays Kits (Invitrogen). A typical sample sizes is 50 µl, and typical detection levels are: IL-1β, 31-2000 pg/ml; IL-10, 15.6-1000 pg/ml; TNFa, 15-1000 pg/ml. These particular cytokines are of interest because they have been associated either with pro-inflammatory (IL-1 and TNF-a) or anti-inflammatory (IL-10) activity during stroke.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific implementations of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

What is claimed:

1. A device comprising:
a fluid-containing chamber housing cells, wherein the cells comprise a first population and a second population;
a porous barrier to which the cells are adhered;
a first channel having an inlet and an outlet, separated from the chamber and the cells by the porous barrier, wherein the first population is located proximate to the first channel, relative to the second population, which is located further away than the first population from the first channel;
a first array of electrodes positioned between the first channel and the porous barrier and aligned along a length of the first channel; and
a second array of electrodes disposed on a fluid facing side of a roof of the fluid-containing chamber, wherein the roof is opposite to and parallel with the porous barrier.

2. The device of claim 1, wherein the first channel comprises cells.

3. The device of claim 1, wherein the first channel is adapted for flowing fluid along the barrier.

4. The device of claim 1, wherein the electrodes are between about 100 µm and 150 µm in diameter.

5. The device of claim 1, wherein the electrodes are configured to measure trans-endothelial electrical resistance.

6. The device of claim 1, wherein the first and second population of cells experience substantially no shear stress when a fluid flows through the first channel.

7. The device of claim 1, wherein the first and second population of cells comprise CNS (central nervous system) cells, cardiac muscle cells, or tumor cells.

8. The device of claim 7, wherein the CNS cells comprise neurons, microglia, astrocytes, oligodendrocytes, or neural progenitors.

9. The device of claim 2, wherein the cells of the first channel comprise a monolayer of muscle cells or endothelial cells along at least one wall of the first channel.

10. The device of claim 1, wherein the first and second population of cells are organized as a three-dimensional culture.

11. The device of claim 1, wherein the first channel and the first population of cells are less than 100 microns apart.

12. The device of claim 1, further comprising a second channel configured for fluid flow, wherein the porous barrier separates the second channel from the chamber and the cells.

13. The device of claim 12, wherein the first channel contains a first fluid and the second channel contains a second fluid.

14. The device of claim 13, wherein the first fluid and the second fluid have different levels of oxygen or oxygen scavenger.

15. The device of claim 12, wherein fluid flow through the first channel and fluid flow through the second channel are individually controllable.

16. The device of claim 1, wherein the porous barrier is sufficiently transparent to allow microscopy of the cells.

17. The device of claim 1, further comprising a proteinaceous coating that is adhered to the porous membrane.

18. The device of claim 1, further comprising immune cells disposed in the channel.

* * * * *